United States Patent [19]
Kolesa et al.

[11] Patent Number: 5,645,553
[45] Date of Patent: *Jul. 8, 1997

[54] SUTURE CLIP APPLIER

[75] Inventors: Michael S. Kolesa, Norwalk; Dominick L. Mastri, Bridgeport, both of Conn.; Wayne P. Young, Brewster, N.Y.; Henry Bolanos, East Norwalk, Conn.

[73] Assignee: United States Surgical Corporation, Norwalk, Conn.

[*] Notice: The portion of the term of this patent subsequent to Oct. 9, 2012, has been disclaimed.

[21] Appl. No.: 440,797

[22] Filed: May 15, 1995

Related U.S. Application Data

[62] Division of Ser. No. 297,333, Aug. 29, 1994, Pat. No. 5,462,558.

[51] Int. Cl.⁶ ..................................... A61B 17/08
[52] U.S. Cl. ..................... 606/157; 606/158; 606/232
[58] Field of Search ..................... 606/232, 157, 606/158

[56] References Cited

U.S. PATENT DOCUMENTS

| | | |
|---|---|---|
| 3,664,345 | 5/1972 | Dabbs et al. . |
| 3,753,438 | 8/1973 | Wood et al. . |
| 3,910,281 | 10/1975 | Klerschka et al. . |
| 3,976,079 | 8/1976 | Samuels et al. . |
| 4,173,067 | 11/1979 | Steiner et al. . |
| 4,201,314 | 5/1980 | Samuels et al. . |
| 4,291,698 | 9/1981 | Fuchs et al. . |
| 4,950,285 | 8/1990 | Wilk . |
| 4,953,384 | 9/1990 | Baillet et al. . |
| 4,955,913 | 9/1990 | Robinson . |
| 5,009,663 | 4/1991 | Broome . |
| 5,053,047 | 10/1991 | Yoon . |
| 5,074,874 | 12/1991 | Yoon et al. . |
| 5,078,731 | 1/1992 | Hayhurst . |
| 5,084,057 | 1/1992 | Green et al. . |
| 5,085,661 | 2/1992 | Moss . |
| 5,100,420 | 3/1992 | Green et al. . |
| 5,105,648 | 4/1992 | Steiner et al. . |
| 5,111,681 | 5/1992 | Yasui et al. . |
| 5,116,340 | 5/1992 | Songer et al. . |
| 5,123,913 | 6/1992 | Wilk et al. . |
| 5,219,359 | 6/1993 | McQuilkin et al. . |
| 5,274,903 | 1/1994 | Grois et al. . |
| 5,282,832 | 2/1994 | Toso et al. . |
| 5,382,254 | 1/1995 | McGarry et al. . |
| 5,382,255 | 1/1995 | Castro et al. . |
| 5,405,354 | 4/1995 | Sarrett . |
| 5,423,860 | 6/1995 | Lizardi et al. . |

FOREIGN PATENT DOCUMENTS

| | | |
|---|---|---|
| 0519704 | 6/1992 | European Pat. Off. . |
| 0538074 | 10/1992 | European Pat. Off. . |
| 0569223 | 5/1993 | European Pat. Off. . |
| 0594003 | 10/1993 | European Pat. Off. . |
| 2682867 | 10/1991 | France . |

*Primary Examiner*—Michael Buiz
*Assistant Examiner*—Mark S. Leonardo

[57] ABSTRACT

A suture fastening device which includes a first member having a base and first and second legs projecting in a lengthwise direction along the base. The legs are parallel to each other and are resiliently biased toward a spaced apart position in relation to each other. A second member is provided and includes an aperture for receiving the first and second legs of the first member. The first and second members are connected by a hinge portion. A suture is held in serpentine fashion by positioning the suture transversely across both legs and locking the first member to the second member by forcing the legs through the aperture.

5 Claims, 7 Drawing Sheets

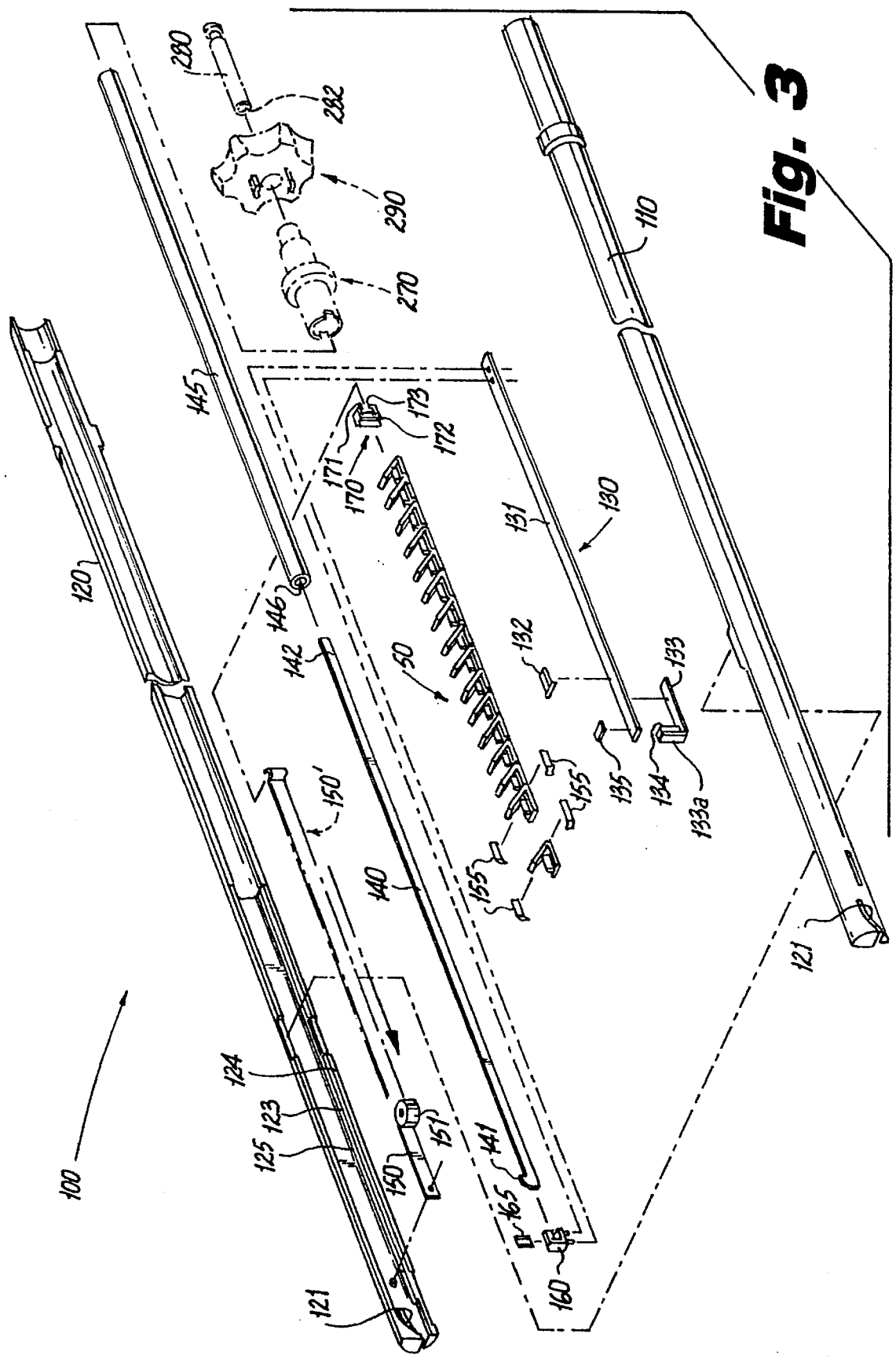

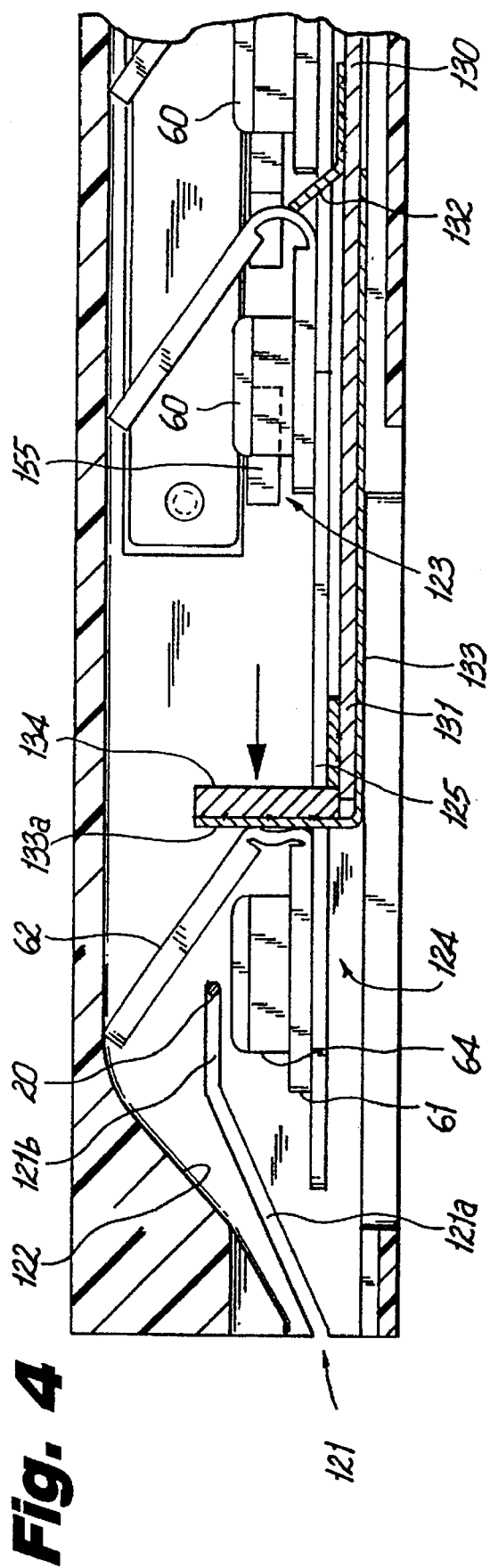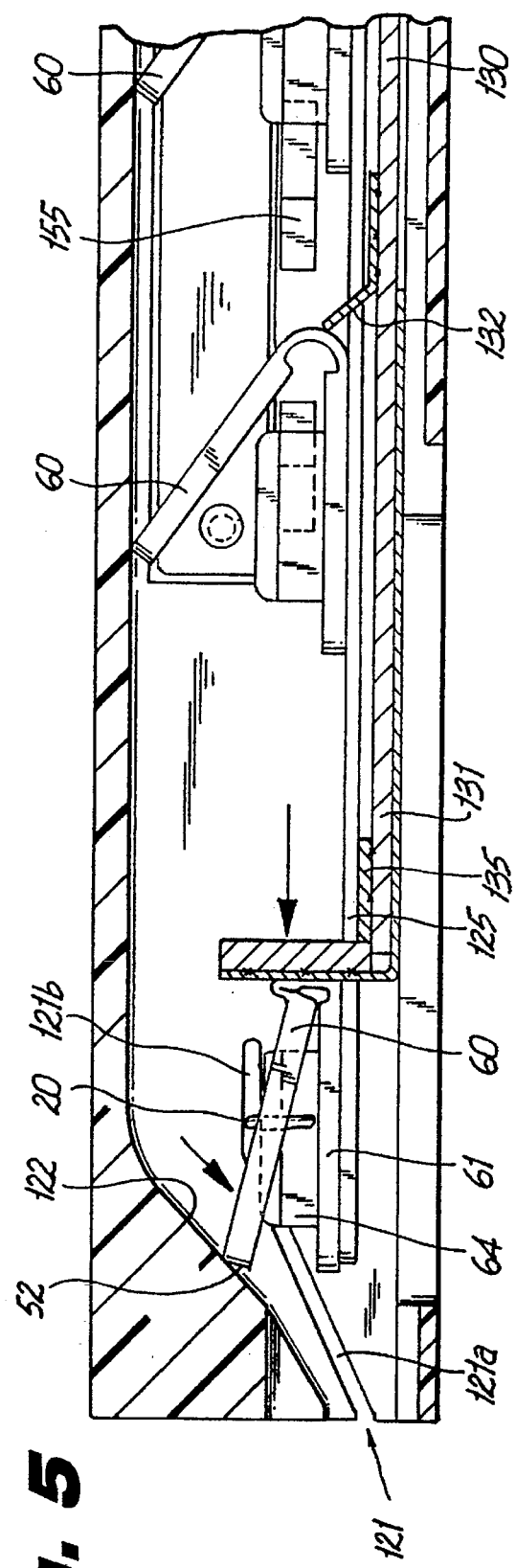

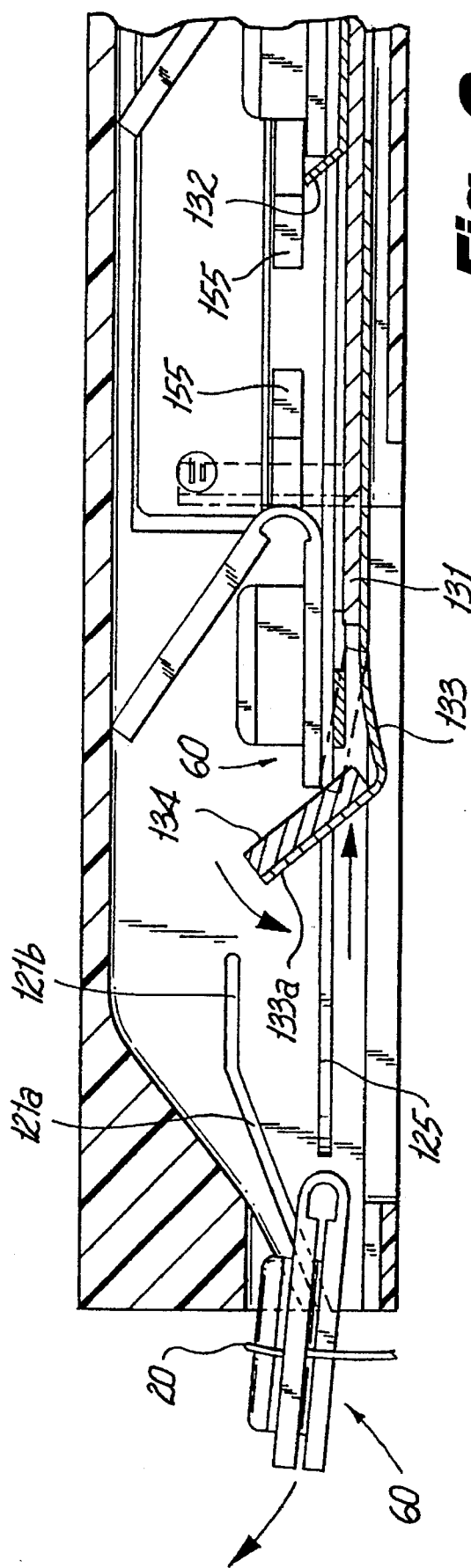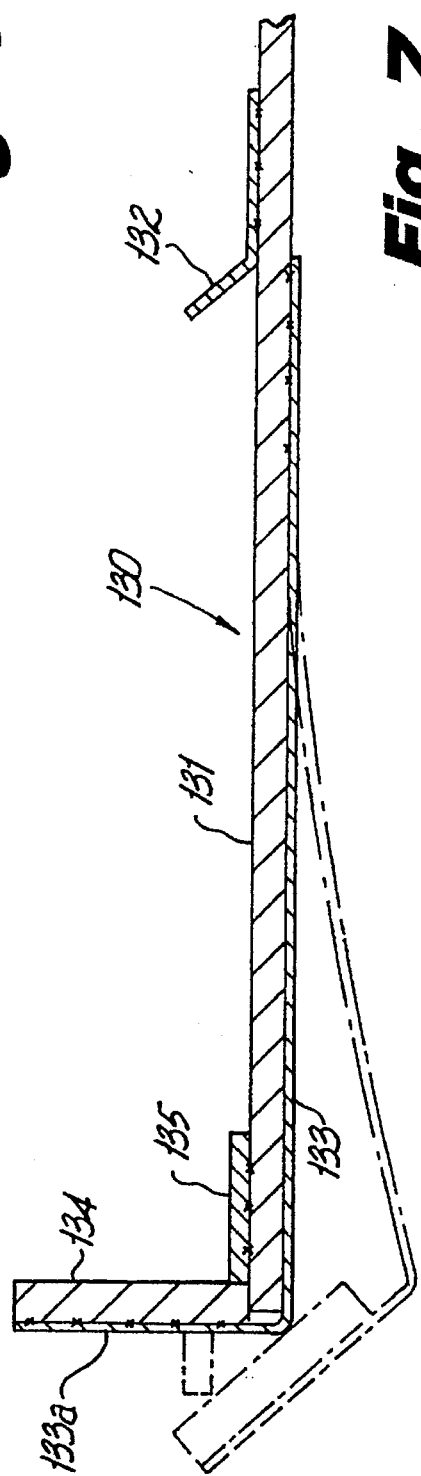

SUTURE CLIP APPLIER

This is a divisional of U.S. application Ser. No. 08/297,333 filed Aug. 29, 1994, now U.S. Pat. No. 5,462,558.

BACKGROUND OF THE INVENTION

1. Field of the Invention

The present invention relates to an apparatus for applying one or more suture clips to a suture during endoscopic and/or laparoscopic surgical procedures or open procedures.

2. Background of the Art

In surgical operations it is often necessary to apply suture retaining clips to sutures. Various clips for holding a suture in a serpentine fashion are disclosed in U.S. Pat. No. 5,282,832, which is herein incorporated by reference in its entirety. What is needed is an instrument for applying such serpentine suture clips during a laparoscopic and/or endoscopic surgical procedure.

In laparoscopic procedures surgery is performed in the interior of the abdomen through a small incision; in endoscopic procedures surgery is performed in any hollow viscus of the body through narrow endoscopic tubes inserted through small entrance wounds in the skin. Often, a small puncture wound is made with a trocar and a cannula is inserted therethrough. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Thus, when the apparatus employed for operations at an insufflated surgical site, the apparatus must be provided with an internal sealing means to prevent passage of gas or other fluids through the interior of the apparatus. Moreover, there should be a seal between the apparatus and the cannula through which it is inserted. The sealing means permits the mechanical movement of the apparatus or its parts while preventing the leak of fluids at the loci of sliding movement. Sealing may be accomplished by closely controlling the dimensional tolerance of the parts during manufacture to insure a close fit, and by the use of viscous sealing gels. Optionally, a sealing block may be employed to provide a seal. Use of a sealing block is disclosed in U.S. Pat. No. 5,100,420, herein incorporated by reference. Moreover, laparoscopic and endoscopic procedures often require the surgeon to act on organs, tissues, and vessels far removed from the incision, thereby requiring that any instruments to be used in such procedures be both long and narrow.

The terms "endoscopic" and "endoscopic portion", among others, as used herein encompass both laparoscopic and endoscopic procedures and refer generally to instruments having elongated and relatively narrow operating portions for inserting into a cannula or a small wound in the skin. These terms should not be construed to limit the present invention to an apparatus for applying suture clips only in conjunction with a cannula. To the contrary, it is believed that the present invention may find use in any procedure where access is limited to a small incision.

SUMMARY OF THE INVENTION

An apparatus is provided herein for applying a suture clip to a suture, which comprises (a) an endoscopic portion having suture receiving means to position a suture transversely to the longitudinal axis of the endoscopic portion, closing means for closing a clip onto a suture positioned within the suture receiving means, pusher means for advancing a suture clip into the closing means, and a tubular housing for enclosing the closing means and the pusher means; and (b) a handle portion including a handle portion housing, and actuation means for actuating the pusher means.

The endoscopic portion includes storing means for storing a plurality of suture clips in a longitudinally extending linear array. The storing means includes at least one longitudinal guide slot in the inner surface of the tubular housing for slidably receiving the suture clips, a longitudinally extending track member for supporting the array of suture clips and biasing means for distally biasing the linear array of suture clips. The biasing means can include a constant force spring and a slidable member, the constant force spring having a distal end fixedly attached to the interior of the tubular housing and a coiled proximal portion, and the slidable member including means to receive the coiled proximal portion of the constant force spring.

The suture receiving means can comprise one or more slots positioned at the distal end of the tubular housing for receiving a suture. The slot preferably has a distal portion which is inclined with respect to the longitudinal axis of the endoscopic portion and a proximal portion which is aligned with the longitudinal axis of the endoscopic portion.

The closing means comprises a camming surface which is inclined with respect to the longitudinal axis of the endoscopic portion.

The pusher means comprises an elongated member slidably mounted within the tubular housing and longitudinally movable between a proximal position and a distal position, a leaf spring member having an angled portion for contacting the proximal end of a suture clip, the leaf spring being movable between a first position wherein the angled portion is in position to contact the proximal end of a suture clip and a second position wherein the angled portion is out of alignment with the suture clip, the angled portion being biased to the first position and movable to the second position when the elongated member is moved from its distal position to its proximal position. The pusher means further includes a drive rod having a distal end and a proximal end and a connector member, the drive rod being slidably mounted in the tubular housing and linearly movable along the longitudinal axis of the tubular housing, the connector member connecting the distal end of the drive rod with the proximal end of the elongated member.

The actuation means includes a trigger which is pivotally mounted to the handle portion housing, and means for transferring pivotal motion of the trigger to linear movement of the drive rod.

The apparatus can further include a pawl and ratchet as indexing means to index movement of the trigger and rotation means to rotate the end scopic portion with respect to the handle portion. The rotation means can include a rotary wheel having a rim extending outside the handle portion housing for actuation by a user's fingers.

BRIEF DESCRIPTION OF THE DRAWINGS

FIG. 3. is an exploded perspective view of the endoscopic portion of the apparatus of the present invention.

FIGS. 4, 5, and 6 are cut away sectional views of the distal end of the endoscopic portion showing the application of a suture clip to a suture.

FIG. 7 is a sectional side view of the clip pusher.

DETAILED DESCRIPTION OF PREFERRED EMBODIMENT(S)

Figure 8:
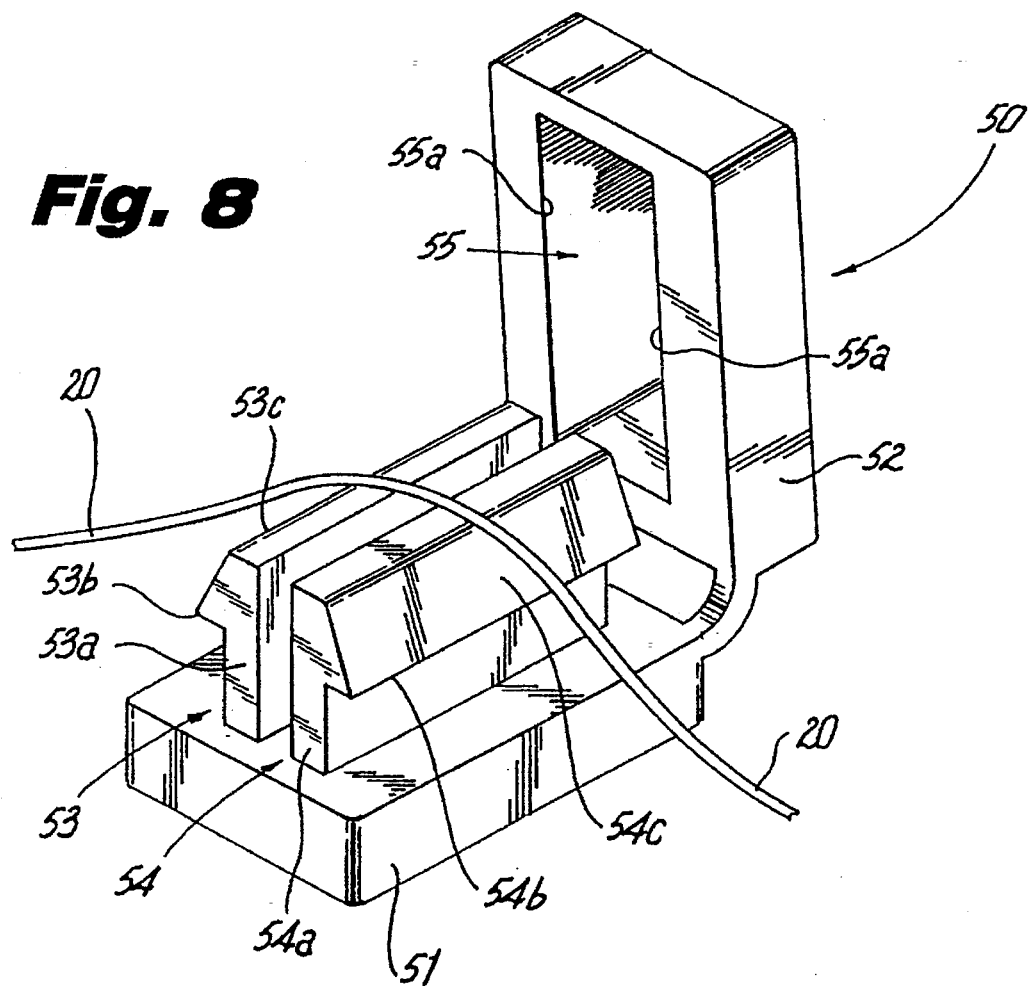
FIGS. 8, and 9 are perspective views showing the suture clip in conjunction with a suture, the suture clip being, respectively, in the open and closed configurations.
Figure 9:
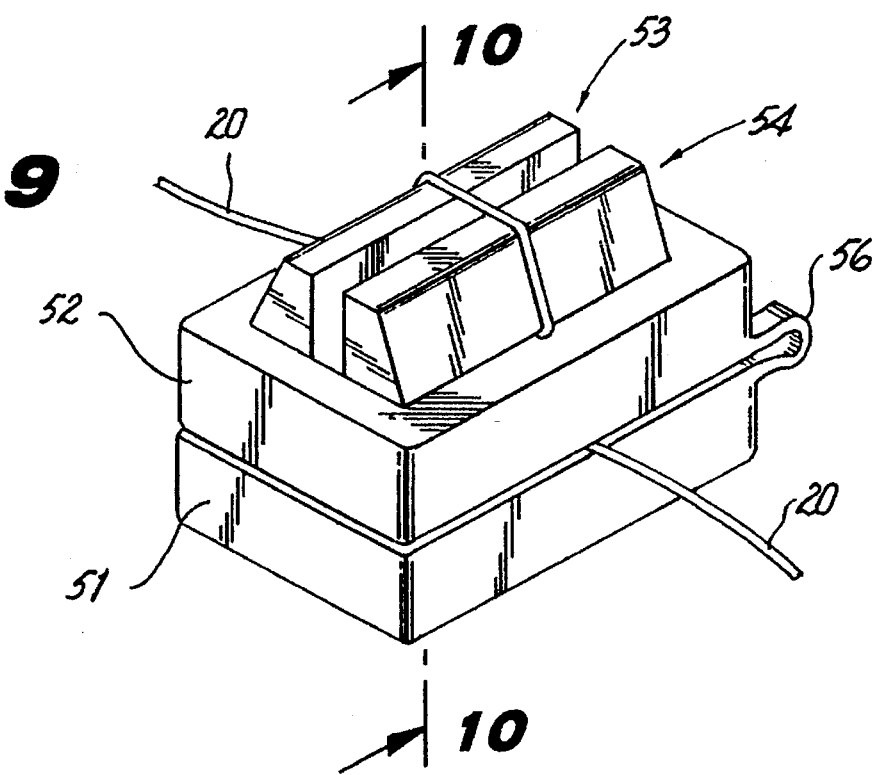
Figure 10:
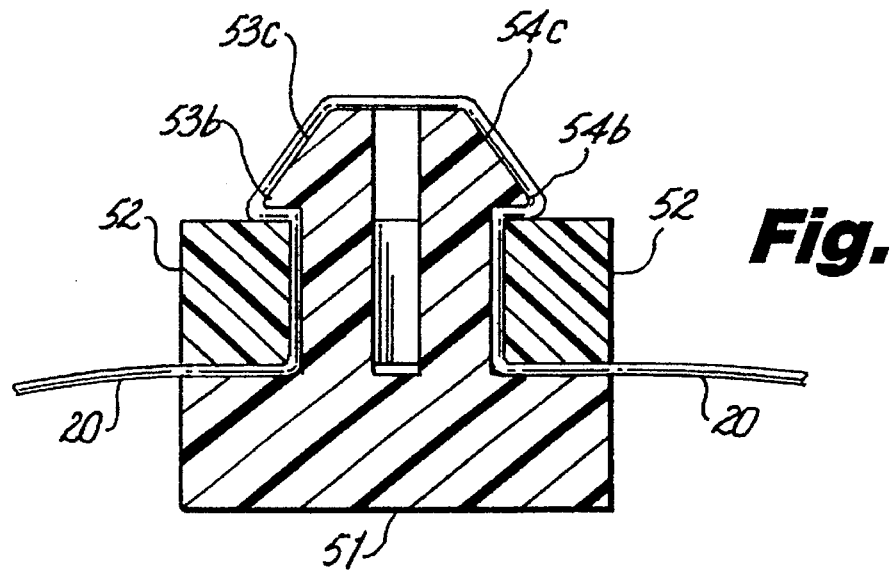
FIG. 10 is a sectional view showing the suture clip in the closed configuration in conjunction with a suture.

A suture clip 50 applied by the present invention is described in U.S. Pat. No. 5,282,832 and is shown in FIGS. 8, 9, and 10. Suture clip 50 comprises a base 51 and retainer 52 which are joined at their edges by flexible hinge 56. Base 51 includes a pair of upstanding spaced apart prongs 53 and 54. Each prong 53 and 54 includes a shaft portion (53a and 54a, respectively) which extends along the base, and a locking barb (53b and 54b, respectively) with a camming surface (53c and 54c, respectively). The retainer 52 includes an aperture 55 having edges 55a.

To secure the clip 50 to a suture 20, one or more strands of the suture is positioned across the prongs 53 and 54 and the retainer 52 is brought down into engagement with prongs 53 and 54. As the retainer 52 is closed upon the base, edges 55a of the aperture cam along surfaces 53c and 54c, thereby forcing the prongs 53 and 54 to resiliently bend inward to accommodate aperture 55. When the retainer 52 and prongs are fully engaged, the prongs 53 and 54 resiliently snap outward to lock the suture clip closed, as shown in FIG. 10. The suture is held in a serpentine fashion.

Figure 12:
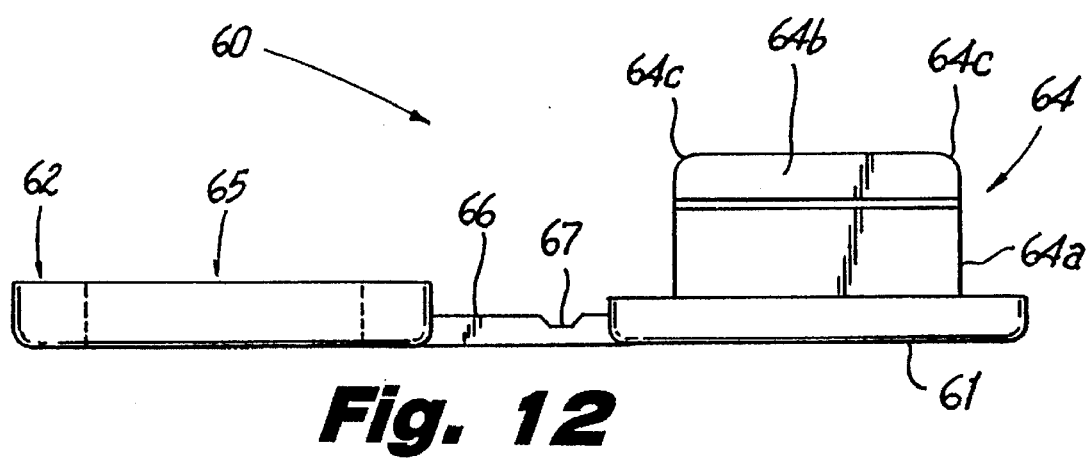
FIG. 12 is an alternative embodiment of the suture clip.

Referring now to FIG. 12, an alternative and preferred embodiment of the suture clip is shown wherein clip 60 includes a base portion 61 and a retainer portion 62 connected by hinge portion 66. The retainer portion 62 includes an aperture 65 for receiving and engaging locking prongs projecting from the base portion 61. Two spaced apart prongs project perpendicularly from base 61, prong 64 being shown in FIG. 12. Both prongs include a shaft portion and a locking barb, shaft portion 64a and locking barb 64b being shown in FIG. 12. Distal and proximal rounded edges 64c facilitate the engagement of the prongs with aperture 65. The hinge portion 66 comprises a thin strip and preferably includes a laterally extending notch 67 which defines a bending region along which hinge portion 65 bends.

The suture clip may be fabricated from any biocompatible material suitable for the purposes described herein. Preferably, the suture clip may be fabricated from bioabsorbable synthetic material such as polymers of lactide, glycolide, caprolactone, p-dioxanone, trimethylene carbonate, and blends and copolymers thereof. Alternatively, the suture clip may be fabricated from a non-absorbable material for permanent placement in the body.

Figure 1:
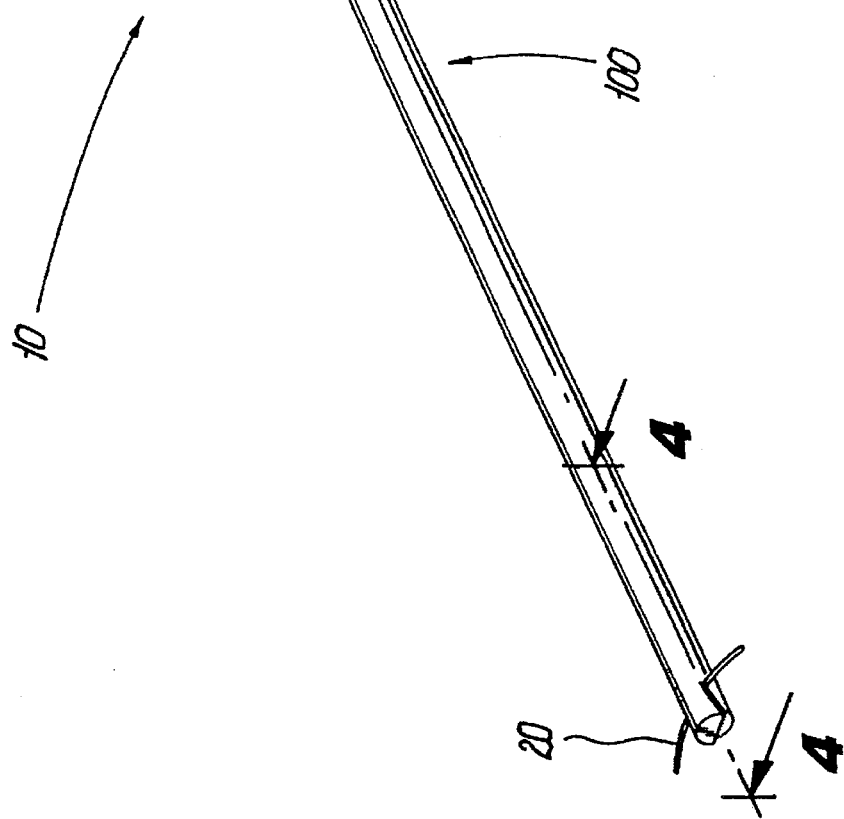
FIG. 1 is a perspective view of the apparatus of the present invention.
Figure 2:
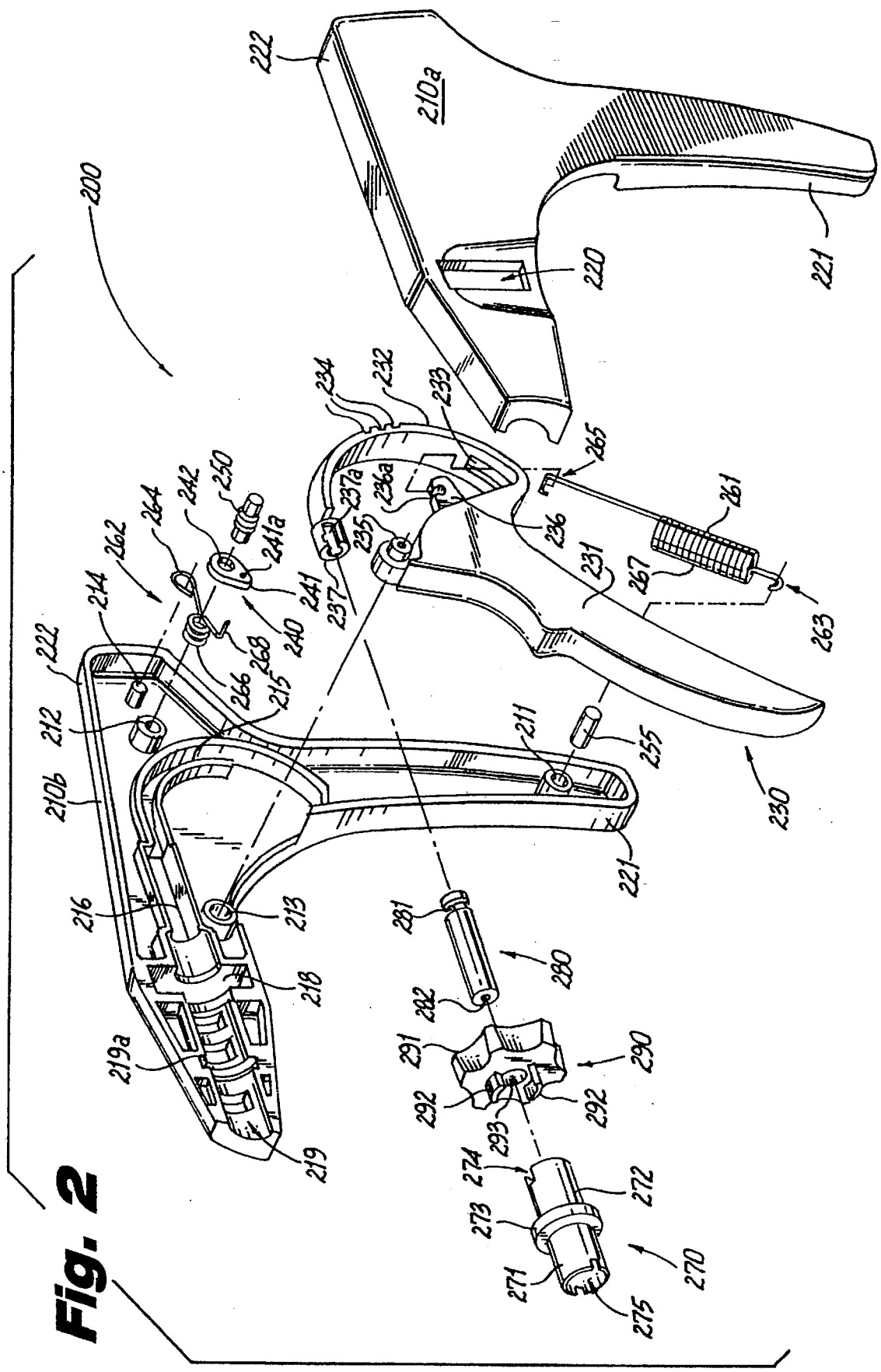
FIG. 2 is an exploded perspective view of the handle portion of the apparatus of the present invention.

Referring to FIG. 1, the clip insertion apparatus 10 of the present invention includes an endoscopic portion 100 and a handle portion 200. The handle portion 200 comprises a left handle body portion 210a and a right handle body portion 210b. Each handle body portion comprises an upper body 222, a lower grip 221 and a slot 220 for permitting a rotary knob to be contacted by the user's finger. The handle body portions 210a and 210b each also possess a configuration of interior walls which define an aperture 211 for receiving dowel pin 255, an aperture 212 for receiving pawl pin 250, a curved slot 215 for receiving curved portion 232 of the trigger 230, aperture 213 for receiving pivot projection 235 of the trigger 230, chamber 216 for receiving coupler 237 of the trigger 230, chamber 218 for receiving rotary wheel 290, axial chamber 219 and circumferential slot 219a for receiving rib 273 of bushing 270. Post 214 extends laterally for holding end 264 of spring 262.

Trigger 230 is for actuating the apparatus and comprises a grip portion 231 which extends downwardly and is adapted to be pressed by the fingers of a user's hand. The trigger pivots around lateral projection 235 which engages aperture 213 and which is rotatably movable therein to pivotally support the trigger 230. Curved portion 232 is a curved strip which is adapted to transfer rotational movement of the trigger into linear movement of the apparatus drive mechanism. Curved portion 232 has ratchet notches 234 on the outer side, and terminates at coupling member 237. Coupling member 237 has a slot means 237a for engaging the proximal end 281 of coupling rod 280. Trigger 230 possesses a projection 236 having a notch 236a for holding hook 265 of spring 261, which is disposed through slot 233 in the curved strip 232.

Trigger spring 261 is an expansion spring having coiled portion 267, a lower hook 263 which engages and is held by pin 255, and an extended upper portion terminating in hook 265. The purpose of spring 261 is to bias the trigger 230 to the non-actuating initial position. That is, to actuate the apparatus the user must press the trigger grip 231 to rotate the trigger against the biasing force of spring 261. When actuating pressure is released, the trigger 230 will return to the initial position.

Pawl 240 has a pointed end 241, an aperture 242 by which it is mounted on pawl pin 250, and an aperture 241a in the pointed end. Pawl spring 262 is a torsion spring which biases the pointed end 241 of the pawl for the purpose of contacting the ratchet notches 234 of the trigger. Pawl spring 262 has a torsion coil 266 mounted on pawl pin 250, a forward end having a lateral hook 268 disposed through aperture 241a of the pointed end 241 of the pawl 240, and a proximal end having a loop 264 which is mounted to post 214. The pawl acting in cooperation with ratchet notches 234 indicates to the user when the clip advancing mechanism has reached certain predetermined positions and allows the user to stop at these positions and relax hand pressure to some extent. It thereby functions as part of an indexing means.

Coupling pin 280 is a generally cylindrical shaped member positioned axially in chamber 219. Coupling pin 280 has a bore 282 in its distal end for receiving and fixedly engaging the proximal end 142 of drive rod 140. Bore 282 may optionally be tapped for screw-in engagement of the drive rod.

Rotary wheel 290 is for turning the endoscopic portion 100 of the apparatus. Rotary wheel 290 is rotatably mounted in chamber 218 and comprises a knurled outer rim 291 which protrudes out through slots 220 to be contacted by a user's finger. Projections 292 extend distally from the rotary wheel 290 and are adapted to engage rear slots 274 of the bushing 270. An axial aperture 293 permits positioning of the coupling rod 280 therethrough.

Bushing 270 is a generally cylindrically shaped member which is rotatably mounted in axial chamber 219 and comprises a distal portion 271, a proximal portion 272, and a rib 273 extending circumferentially around the bushing 270. Proximal notches 274 are configured and dimensioned to receive projections 292 of the rotary wheel. The engagement of projections 292 and notches 274 permits rotary motion of wheel 290 to be transferred to bushing 270.

Bushing 270 has an axial bore 275 to permit positioning therethrough of the drive rod 140.

The endoscopic portion 100 of the apparatus includes cover tube 101 which comprises a left portion 110 of the cover tube 101 and right portion 120 of cover tube 101. Left and right portions 110 and 120 are elongated members which can be assembled to form an enclosure for the operating instrumentation in the endoscopic portion. The left and right portions 110 and 120 each have (as illustrated on the right portion 120 and shown more clearly in FIGS. 4 to 6) a suture receiving slot 121 at the distal end, a distal camming surface 122, an upper longitudinally extending slot 123, and a lower longitudinally extending slot 124. The suture receiving slot 121 is configured to receive a suture 20 oriented laterally with respect to the endoscopic portion 100. This is shown, for example, in FIG. 1. The suture receiving slot 121 has a distal upwardly inclined portion 121a (i.e. inclined with respect to the longitudinal axis of the instrument) and a proximal section 121b which is in line with the longitudinal axis of the instrument. The camming surface slopes down (as shown) so as to provide means for closing the clip 60 as the clip 60 advances. A plurality of suture clips 60 are stored in the cover tube 101 in a longitudinally oriented row. The upper slot 123 and lower slot 124 and separated by longitudinal ridge 125 which constitutes a clip track floor along which the row of clips extends and is adapted to allow slidable movement of the clips along the direction of the axis of the endoscopic portion 100. Lower slot 124 runs parallel to upper slit 123 and is adapted to receive pusher lever 131 of the clip pushing means 130.

The clip pushing means 130 (shown in FIGS. 3, 4, 5, 6, and 7) comprises elongated pusher lever 131 which is slidably mounted in lower slot 124, lead push spring 132 which is biased upward and is adapted to engage the rear edge of the distal-most clip in the linear clip array and to position the clip for advancement, push spring 133 which is a leaf spring mounted to the bottom surface of the pusher lever at the distal end thereof, and finger block 134, which is mounted to an upturned distal end 133a of the pusher spring 133. Push spring 133 and finger block 134 are adapted to bend out of the way on the return stroke of the pushing means to permit the next clip in line to occupy the distal-most position. A backstop plate 135 may optionally be included to provide a backstop support to fingersblock 134 when advancing a clip for closure.

The clip in the distal-most position is releasably held by leaf retainer springs 155. Behind the proximal-most clip is a slider 170 having two rearward (i.e. proximal) pointing projections 171 and 172 which define a notch 173 between them. The notch is adapted to receive and engage a coiled constant force spring 150.

Constant force spring 150 comprises a resilient metal strip fixedly mounted at its distal end to the inner surface of the cover tube. Constant force spring 150 includes a resilient coil 151 which is biased by a constant torque to a curled up configuration. Initially, constant force spring 150 is in an extended configuration as shown by constant force spring 150' in FIG. 3. As clips are applied to tissue the line of clips advances because coil 151, being cradled in notch 173, gradually curls up, thereby causing slider 170 to apply a constant forward biasing force to the proximal-most clip.

Pusher fitting 160 includes a cover plate 165 and is configured and dimensioned so as to receive the distal end 141 of the drive rod 140. Pusher fitting 160 is fixedly mounted to the proximal end of the pusher lever bar 131.

Thus, when pusher fitting 160 is advanced by distal movement of the drive rod 140, the pusher lever bar 131 is also distally advanced to urge forward the distal-most clip for closure.

Drive rod 140 is slidably disposed within bore 146 of stiffening tube 145, which is located within the cover tube to maintain rigidity of the endoscopic portion 100. The drive rod 140 has an upward distal end 141 for engagement with the pusher fitting 160, and a proximal end 142 which optionally may be threaded for screw-in engagement with tapped bore 282 of the coupling pin 280.

Referring to FIGS. 4, 5, and 6, the operation of the apparatus is illustrated. A suture 20 is positioned at the proximal end of slot 121. The clip pusher 130 is positioned such that the distal portion 133a of the pusher spring 133 is in contact with the proximal end of clip 60. Clip 60 rests on clip track floor 125. The clip pusher is advanced, thereby pushing clip 60 into the camming surface 122. As shown in FIG. 5, further advancement of the clip 60 moves the retainer portion 52 into sliding contact with camming surface 122, thereby forcing retainer 52 into engagement with the prongs 53 and 54 of the base 51. The suture clip 60 is thereafter released, as shown in FIG. 6 and the clip pusher 130 is proximally withdrawn. Upon proximal withdrawal, finger 134 is forced downward by contact with the leading edge of the next clip. The clip pusher spring 133 bends to permit the distal portion 133a to ride underneath the next clip. Upon being moved proximal to the next clip, the distal end 133a of the clip pusher flips upward and moves into position for the next pushing cycle.

As each distal-most clip is advanced, the next clip in line is moved up into the distal-most position by lead push spring 132. Leaf retainer springs 155 maintain the distance between the distal-most clip and the next clip.

Figure 11:
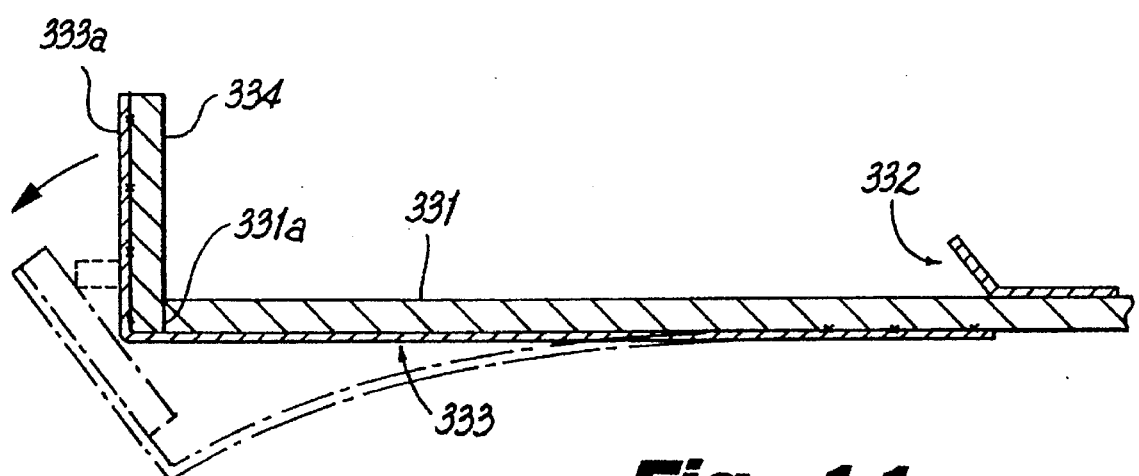
FIG. 11 is an alternative embodiment of the clip pusher of FIG. 7.

FIG. 11 discloses an alternative pusher embodiment 330 of the pusher of FIG. 7. Pusher 330 comprises an elongated pusher lever 331, lead push spring 332, push spring 333 and finger block 334 mounted to upturned distal end 333a of the pusher spring 333. The finger block 334 of the alternative embodiment abuts the distal end surface 331a of the pusher lever. As with embodiment 130 of the pusher, pusher spring 330 bends to permit the distal portion 333a and finger block 334 to ride underneath the next clip when pusher 330 is moved proximally.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A suture fastening device which comprises:
a) a first member having a lengthwise extension defined by its longest side and including a base portion, first and second legs projecting from said base portion and extending lengthwise along the base portion, said first and second legs parallel to each other along the lengthwise direction of the base, and being resiliently biased toward a spaced apart position from each other and movable toward each other in response to force applied thereto;
b) a second member having a lengthwise extension defined by its longest side, said second member having an aperture for receiving said first and second legs of said first member; and c) a hinge portion connecting said first and second member, said hinge portion comprising a thin strip.

2. The suture fastening device of claim 1 wherein said hinge portion includes a notch which defines a bending region.

3. The suture fastening device of claim 1 wherein said first and second legs include rounded edges.

4. The suture fastening device of claim 1 wherein said suture fastening device is fabricated as a single piece.

5. The suture fastening device of claim 4 wherein said suture fastening device is fabricated from a synthetic bioabsorbable material.

* * * * *